United States Patent
Lee et al.

(10) Patent No.: US 9,173,616 B2
(45) Date of Patent: Nov. 3, 2015

(54) METHOD AND APPARATUS FOR PROVIDING THREE-DIMENSIONAL (3D) IMAGE

(71) Applicant: SAMSUNG ELECTRONICS CO., LTD., Suwon-si (KR)

(72) Inventors: Kang Eui Lee, Seoul (KR); Jong Ha Lee, Hwaseong-si (KR); Kwang Eun Jang, Busan (KR); Young Hun Sung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 100 days.

(21) Appl. No.: 14/030,257

(22) Filed: Sep. 18, 2013

(65) Prior Publication Data

US 2014/0112435 A1    Apr. 24, 2014

(30) Foreign Application Priority Data

Oct. 22, 2012 (KR) .................. 10-2012-0117295

(51) Int. Cl.
*A61B 6/02*  (2006.01)
*G06T 11/00*  (2006.01)
*G06T 15/08*  (2011.01)

(52) U.S. Cl.
CPC ............. *A61B 6/022* (2013.01); *G06T 11/008* (2013.01); *G06T 15/08* (2013.01); *G06T 2211/436* (2013.01)

(58) Field of Classification Search
USPC ................... 378/1, 38, 39, 40, 41
See application file for complete search history.

(56) References Cited

U.S. PATENT DOCUMENTS

| | | | |
|---|---|---|---|
| 2006/0067464 A1* | 3/2006 | Clinthorne et al. | 378/38 |
| 2007/0286470 A1 | 12/2007 | Bernard et al. | |
| 2008/0025592 A1 | 1/2008 | Jerebko et al. | |
| 2009/0022264 A1 | 1/2009 | Zhou et al. | |
| 2012/0230467 A1* | 9/2012 | Katsumata et al. | 378/19 |

FOREIGN PATENT DOCUMENTS

| | | |
|---|---|---|
| JP | 2007-209758 A | 8/2007 |
| JP | 4152765 B2 | 7/2008 |
| KR | 10-2010-0054973 A | 5/2010 |
| KR | 10-2011-0016527 A | 2/2011 |
| KR | 10-2011-0020969 A | 3/2011 |
| KR | 10-2011-0104170 A | 9/2011 |

* cited by examiner

*Primary Examiner* — Nicole Ippolito
*Assistant Examiner* — Hanway Chang
(74) *Attorney, Agent, or Firm* — Sughrue Mion, PLLC (57) ABSTRACT

Provided is a method and apparatus for providing a three-dimensional (3D) image. A plurality of first projection images may be created by detecting X-rays which are emitted toward an object at different angles. A plurality of second projection images with respect to a partial volume of the object may be created by applying a forward projection and interpolation to at least one of the plurality of first projection images. A left image and a right image may be selected from among the plurality of second projection images, and the selected left image and right image may be displayed for a user as a 3D projection image.

20 Claims, 5 Drawing Sheets

PROJECTION IMAGE CAPTURING

RECONSTRUCTION

PARTIAL VOLUME REPROJECTION

VIEW INTERPOLATION PROCESSING

FIG. 5

METHOD AND APPARATUS FOR PROVIDING THREE-DIMENSIONAL (3D) IMAGE

CROSS-REFERENCE TO RELATED APPLICATION

This application claims priority from Korean Patent Application No. 10-2012-0117295, filed on Oct. 22, 2012, in the Korean Intellectual Property Office, the disclosure of which is incorporated herein by reference in its entirety.

BACKGROUND

1. Field

Exemplary embodiments relate to a method and apparatus for providing a three-dimensional (3D) image.

2. Description of the Related Art

A digital breast tomosynthesis (DBT) refers to an apparatus which may be used for acquiring an X-ray projection image of breast from a limited angle and reconstructing a three-dimensional (3D) volume of breast tissue based on the acquired X-ray projection image. For example, the DBT may refer to an apparatus which may be used for creating a 3D image which represents a portion of a body of an object by digitizing multiple X-rays.

To diagnose a state of tissue which may include breast cancer by using the reconstructed volume of breast tissue, a diagnostician has generally so far observed slices of recovered volume. In the case of the above method, the diagnostician may be required to perform a diagnosis while performing an imaging correlation between slices in his mind, and may be required to perform the diagnosis by using a large number of slice images. In addition, in the case of using a slice image, tissue which is twisted on a detector plane may not be identifiable due to depth blurring.

SUMMARY

According to an aspect of one or more exemplary embodiments, there may be provided a method for providing a three-dimensional (3D) image, the method including: acquiring a plurality of first projection images which are created by detecting, by using an X-ray detector, X-rays which are emitted from an X-ray source toward an object; generating a 3D volume which represents the object by using the plurality of first projection images; creating a plurality of second projection images by applying a forward projection to the 3D volume; and displaying the plurality of second projection images by using a 3D display.

The generating the 3D volume may include: generating a full volume of the object by using the plurality of first projection images; and dividing the full volume into at least one partial volume. The 3D volume may be selected from the at least one partial volume.

The dividing the full volume may include using at least one plane in parallel with a detector plane.

The plurality of first projection images may be created by detecting, by using the X-ray detector, the X-rays which are emitted from the X-ray source toward the object at an angle from within a predetermined angular range.

At least one of a number of first projection images which comprise the plurality of first projection images and the predetermined angular range may be determined based on a radiation dose which relates to the object.

The creating the plurality of second projection images may include creating at least one reprojection image by applying at least one of the forward projection and an interpolation to at least one of the plurality of first projection images. The plurality of second projection images may include the plurality of first projection images and the at least one reprojection image.

The plurality of second projection images may include a left image which is observable by using a left eye of a user and a right image which is observable by using a right eye of the user.

Each of the left image and the right image may be adjusted such that the 3D volume is recognizable by viewing the left image and the right image based on a baseline length of the user.

Each of the left image and the right image may be adjusted such that the 3D volume is recognizable by viewing the left image and the right image based on a thickness of the 3D volume.

According to another aspect of one or more exemplary embodiments, there may be provided an apparatus for providing a 3D image, the apparatus including: an X-ray source which emits X-rays toward an object; an X-ray detector which detects the emitted X-rays; a controller which generates a 3D volume which represents the object by using a plurality of first projection images that is created by detecting, by using the X-ray detector, the X-rays emitted from the X-ray source toward the object at different angles, and which creates a plurality of second projection images by applying a forward projection to the 3D volume; and an output unit which outputs the plurality of second projection images.

The controller may generate a full volume of the object by using the plurality of first projection images and may divide the full volume into at least one partial volume. The 3D volume may be selected from the at least one partial volume.

The controller may generate the at least one partial volume by dividing the full volume by using at least one plane in parallel with a detector plane.

The plurality of first projection images may be created by detecting, by using the X-ray detector, the X-rays which are emitted from the X-ray source toward the object at an angle from within a predetermined angular range.

The controller may determine at least one of a number of first projection images which comprise the plurality of first projection images and the predetermined angular range based on a radiation dose which relates to the object.

The controller may create at least one reprojection image by applying at least one of the forward projection and an interpolation to at least one of the plurality of first projection images. The plurality of second projection images may include the plurality of first projection images and the at least one reprojection image.

The plurality of second projection images may include a left image which is observable by using a left eye of a user and a right image which is observable by using a right eye of the user.

The controller may adjust each of the left image and the right image such that the 3D volume is recognizable by viewing the left image and the right image based on a baseline length of the user.

The controller may adjust each of the left image and the right image such that the 3D volume is recognizable by viewing the left image and the right image based on a thickness of the 3D volume.

BRIEF DESCRIPTION OF THE DRAWINGS

The above and other aspects of exemplary embodiments will become apparent and more readily appreciated from the following detailed description of certain exemplary embodiments, taken in conjunction with the accompanying drawings of which.

DETAILED DESCRIPTION

Reference will now be made in detail to exemplary embodiments, examples of which are illustrated in the accompanying drawings, wherein like reference numerals refer to the like elements throughout. Exemplary embodiments are described below in order to explain the present disclosure by referring to the figures.

The terms "reconstructed" and "recovered" may be replaced with each other and thereby be used throughout the specification.

Figure 1:
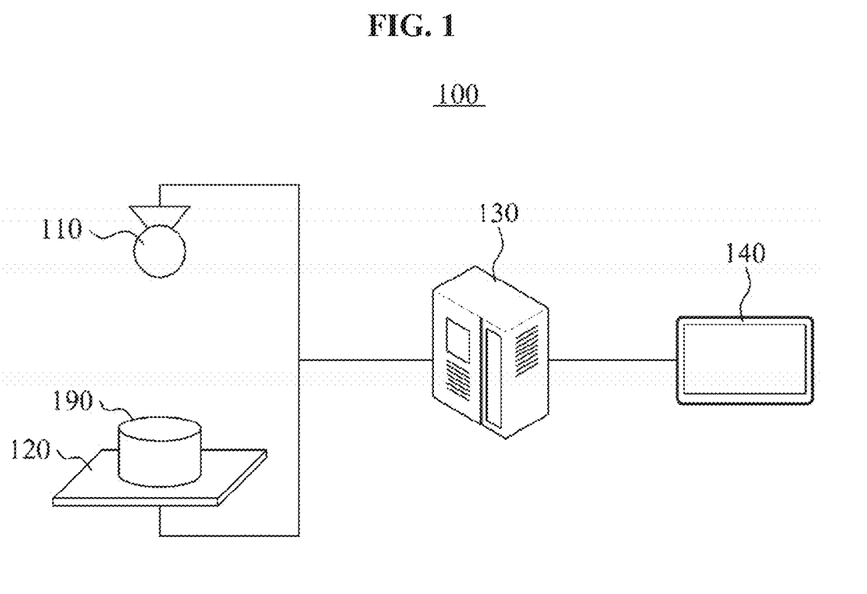
FIG. 1 is a diagram which illustrates a three-dimensional (3D) image providing apparatus and an object, according to one or more exemplary embodiments.

FIG. 1 is a diagram which illustrates a three-dimensional (3D) image providing apparatus 100 and an object 190, according to one or more exemplary embodiments.

Referring to FIG. 1, the 3D image providing apparatus 100 may include an X-ray source 110, an X-ray detector 120, a controller 130, and an output unit 140.

The 3D image providing apparatus 100 may be a medical diagnostic apparatus. For example, the 3D image providing apparatus 100 may be a digital breast tomosynthesis (DBT).

The X-ray source 110 may emit X-rays toward the object 190. The object 190 may be a patient or a body part of the patient, such as, for example, a breast of the patient.

The X-ray detector 120 may detect the X-rays which are emitted toward the object 190.

The X-ray detector 120 and/or the controller 130 may create a projection image based on the detected X-rays.

Detection of the X-rays may be expressed by Equation 1.

$$I_0 = I \cdot e^{-\mu x}$$ [Equation 1]

In Equation 1, I denotes an intensity of X-rays which are output from the X-ray source 110, $\mu$ denotes a unique attenuation coefficient of a material, X denotes a density of the material, and $I_0$ denotes an intensity of the X-ray detected by the X-ray detector 120.

The controller 130 may generate a 3D volume which represents the object 190, based on the created projection image.

The controller 130 may create a stereoscopic image with respect to the generated 3D volume. The stereoscopic image may be a stereoscopic projection image. The stereoscopic image may provide 3D image information associated with the object 190 to a user of the 3D image providing apparatus 100. The stereoscopic image may be a 3D image which provides information for use with respect to performing a medical diagnosis of the object 190. The user may be a user of the 3D image providing apparatus 100, for example, an observer or a diagnostician who diagnoses tissue of a patient.

The output unit 140 may output the stereoscopic image. The output unit 140 may be, for example, a display which is capable of displaying a 3D image for the user. For example, when the user wears shutter glasses, the output unit 140 may be synchronized with the shutter glasses and may alternatingly output a left-eye image which is observable by using a left eye of the user and a right-eye image which is observable by using a right eye of the user. In particular, the left-eye image may be an image which is output when a shutter of a right lens of the shutter glasses is closed, and the right-eye image may be an image which is output when a shutter of a left lens of the shutter glasses is closed. In the above example, the stereoscopic image may be an image in which two projection images are alternatingly repeated.

When the user wears polarized glasses, the output unit 140 may output an image which is observable via a left polarized lens, for example, an image that passes through filtering of the left polarized lens, and an image which is observable via a right polarized lens, for example, an image that passes through filtering of a right polarized lens. Alternatively, the output unit 140 may include two displays. The user may view a left-eye image and a right-eye image that are output from the two displays, respectively, by placing the left eye and the right eye of the user to be close to the two displays, respectively. In the above example, the stereoscopic image may include two projection images.

Figure 2:
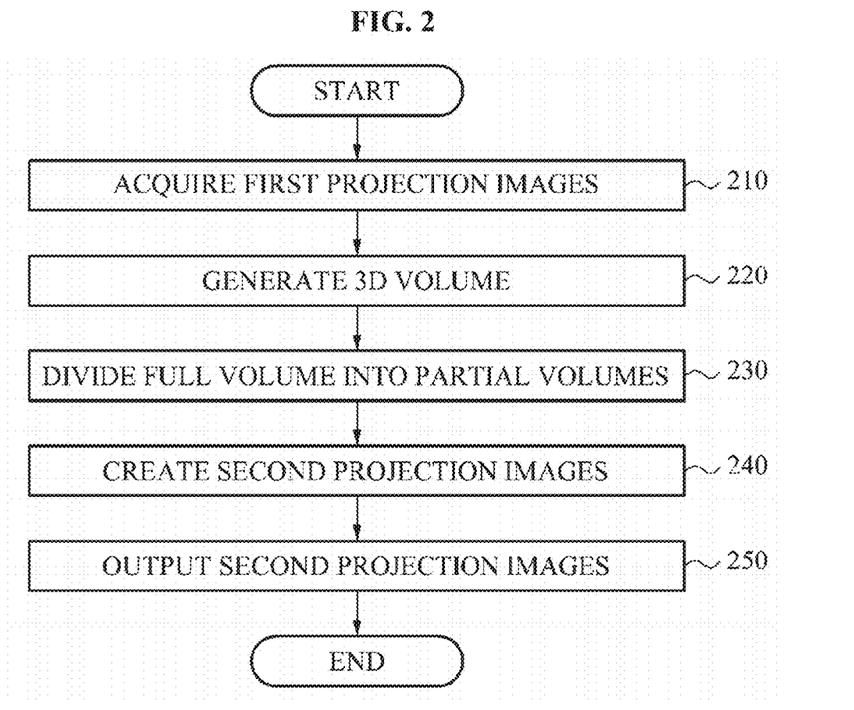
FIG. 2 is a flowchart which illustrates a method for providing a 3D image, according to one or more exemplary embodiments.

FIG. 2 is a flowchart which illustrates a method for providing a 3D image, according to one or more exemplary embodiments.

In operation 210, the controller 130 may acquire a plurality of first projection images.

The plurality of first projection images may be created by detecting, by using the X-ray detector 120, X-rays which are emitted from the X-ray source 110 toward the object 190 at different angles. For example, the plurality of first projection images may be images which are acquired through capturing. A method for acquiring the plurality of first projection images will be further described with reference to FIG. 3.

In operations 220 and 230, the controller 130 may generate a 3D volume which represents the object 190 by using the plurality of first projection images.

In operation 220, the controller 130 may generate a full volume of the object 190 by using the plurality of first projection images. The full volume may be three-dimensionally expressed. For example, operation 220 may be regarded as an operation of reconstructing the 3D volume which represents the object 190 by using the plurality of first projection images.

In operation 230, the controller 130 may divide the full volume into at least one partial volume. The 3D volume may be selected from the at least one partial volume.

In operation 240, the controller 130 may create a plurality of second projection images by applying a forward projection to the 3D volume. The controller 130 may include a forward projection module which generates the forward projection. By application of the forward projection, the plurality of second projection images that are projection images with respect to only a portion of the full volume may be created.

In operation 250, the controller 130 may output the plurality of second projection images by using the output unit 140. The plurality of second projection images may include a left image and a right image. The left image may be a left-eye image that is observable by using a left eye of the user by using the 3D image providing apparatus 100. The right image may be a right-eye image observable by using a right eye of the user. For example, the left image and the right image may constitute a stereoscopic image.

As a result of the above output, the 3D volume may be three-dimensionally visualized. By creating the plurality of second projection images with respect to a portion of the full volume, it may be possible to reduce a frequency of an occurrence of a phenomenon that causes tissue to appear to overlap in a projection image. By outputting the plurality of second projection images as a stereoscopic image, it may be possible to provide a further enhanced diagnostic environment to the user.

Figure 3:
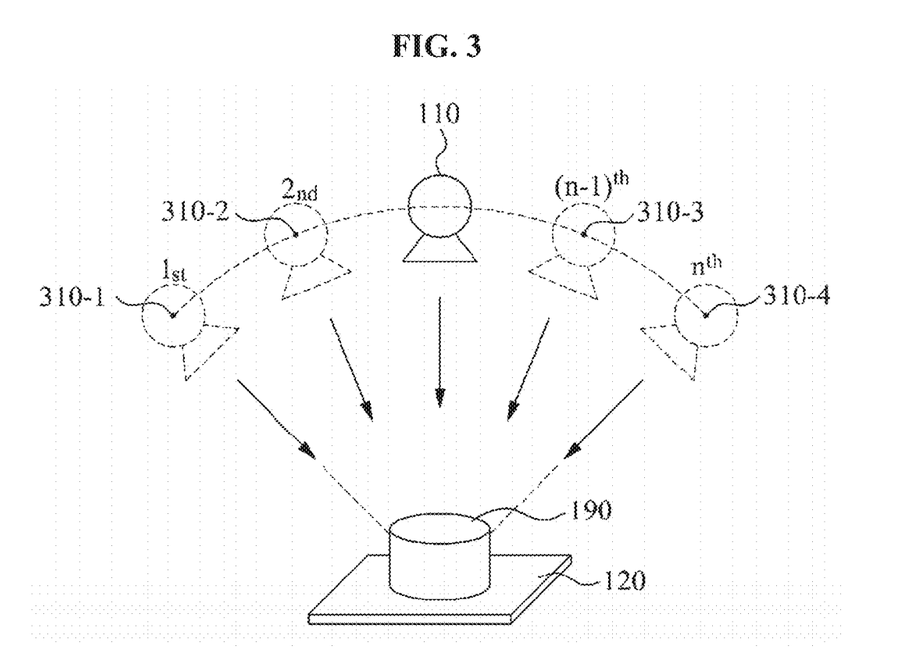
FIG. 3 is a diagram which illustrates a method for acquiring a projection image, according to one or more exemplary embodiments.

FIG. 3 is a diagram which illustrates a method for acquiring a projection image, according to one or more exemplary embodiments.

Each of a plurality of first projection images may be created by detecting, by using the X-ray detector 120, X-rays which are emitted from the X-ray source 110 toward the object 190 at an angle from within a predetermined angular range.

Referring to FIG. 3, the predetermined angular range is indicated by a dotted line. The range indicated by the dotted line may represent an area to which an X-ray is actually emitted.

The X-ray source 110 may emit X-rays toward the object 190 while moving within the predetermined angular range. For example, the X-ray source 110 may sequentially emit X-rays toward the object 190 at a plurality of positions, for example, a first position 310-1, a second position 310-2, an $(n-1)^{th}$ position 310-3, and an $n^{th}$ position 310-4.

The X-ray detector 120 may detect the emitted X-rays at each of the plurality of positions. A first projection image may be created based on the X-rays detected by at least one of the X-ray detector 120 and the controller 130.

When the object 190 is a living thing and/or a body part of a living thing, a radiation dose which relates to the object 190 may be medically or legally limited. Accordingly, at least one of the number of first projection images which comprise the plurality of first projection images and the predetermined angular range may be determined based on the radiation dose which is to be irradiated toward the object 190. For example, when the plurality of first projection images is to be created at predetermined intervals or angles, a predetermined range of an angle may be determined based on the radiation dose which is to be irradiated toward the object 190. Alternatively, when a maximum angle and a minimum angle of the first projection images are determined, the number of first projection images to be acquired between the maximum angle and the minimum angle may be determined based on the radiation dose which is to be irradiated toward the object 190.

Figure 4:
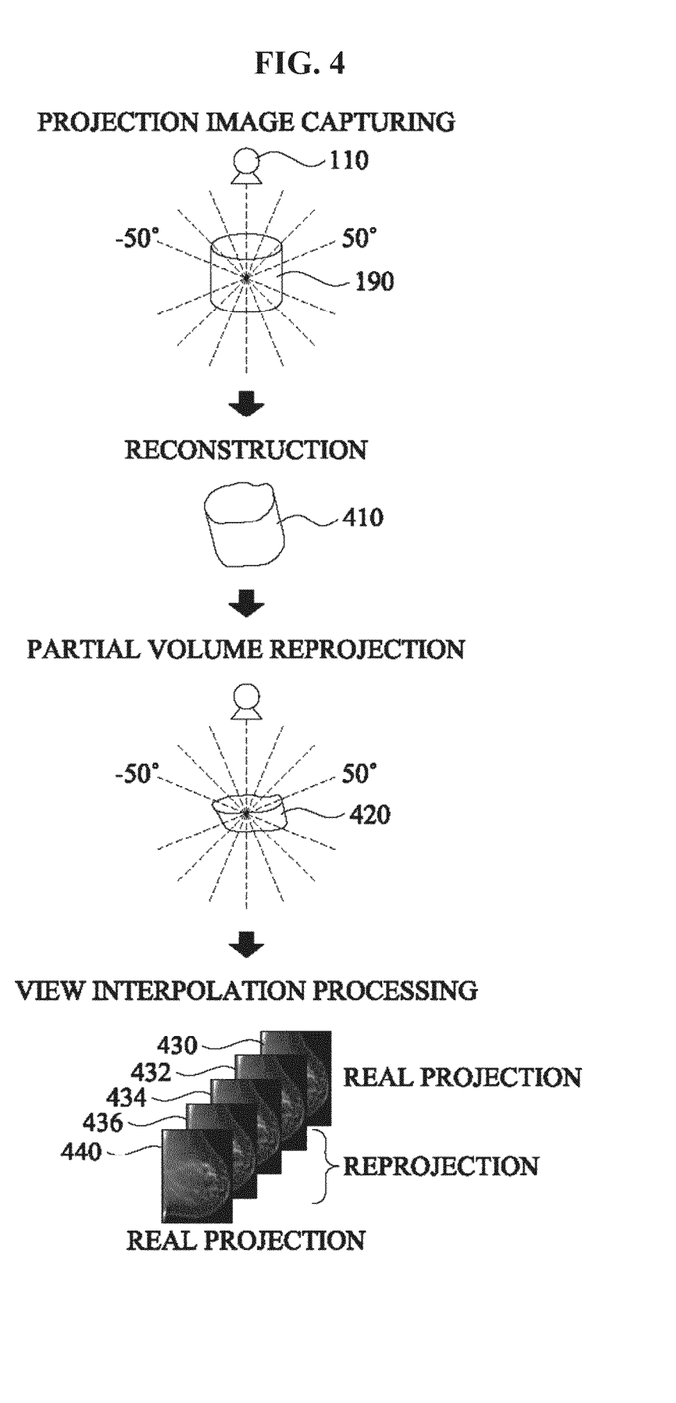
FIG. 4 is a diagram which illustrates a procedure for creating a second projection image, according to one or more exemplary embodiments.

FIG. 4 is a diagram which illustrates a procedure of creating a second projection image, according to one or more exemplary embodiments.

A plurality of first projection images may be created by performance of projection image capturing in operation 210 of FIG. 2. Referring to FIG. 4, the object 190 may be photographed at an angle within the range of −50 degrees to 50 degrees by the X-ray source 110.

A reconstructed 3D volume 410 may represent a full volume of the object 190, which is generated in operation 220.

A partial 3D volume 420 may represent a partial volume of the object 190, which is generated in operation 230. In FIG. 4, a second projection image may be provided with respect to respective angles which fall within the range of −50 degrees to 50 degrees.

View interpolation processing may be one example of a method for creating a plurality of second projection images.

The plurality of second projection images may include at least one real projection image and at least one reprojection image. The at least one real projection image may indicate a portion of or all of the plurality of first projection images which are acquired in operation 210. Alternatively, the at least one real projection image may indicate a portion of or all of a plurality of images which are created by applying a forward projection to the 3D volume in operation 240. A reprojection image may indicate an image which is created by applying the forward projection to the 3D volume in operation 240.

Referring to FIG. 4, a first real projection image 430 and a second real projection image 440 are provided as real projection images, and a first reprojection image 432, a second reprojection image 434, and a third reprojection image 436 are provided as reprojection images.

Each of the plurality of first projection images may be a slice of a partial volume. The plurality of first projection images may be a slab that includes a set of slices.

The plurality of second projection images may include at least one reprojection image which is created by using view interpolation. The controller 130 may additionally create at least one reprojection image by applying view interpolation to the plurality of first projection images and the plurality of reprojection images. Accordingly, the plurality of second projection images may include a first projection image, a reprojection image which is created via the forward projection, and a reprojection image which is created via view interpolation. The controller 130 may refine a reprojection image which is created via the forward projection by applying interpolation. For example, the aforementioned interpolation may be regarded as a process of performing refinement with respect to the second projection image to be displayed for the user.

Operation 240 of FIG. 2 may include an operation of creating at least one reprojection image by applying at least one of the forward projection and interpolation to the plurality of first projection images. The plurality of second projection images may include the plurality of first projection images and the plurality of reprojection images.

By performance of the forward projection and the interpolation, the plurality of second projection images may be created at an outer angle of an area to which the X-ray is actually emitted. Further, as compared to a projection image which is created via the real projection, projection images having an improved signal to noise ratio (SNR) may be provided.

Figure 5:
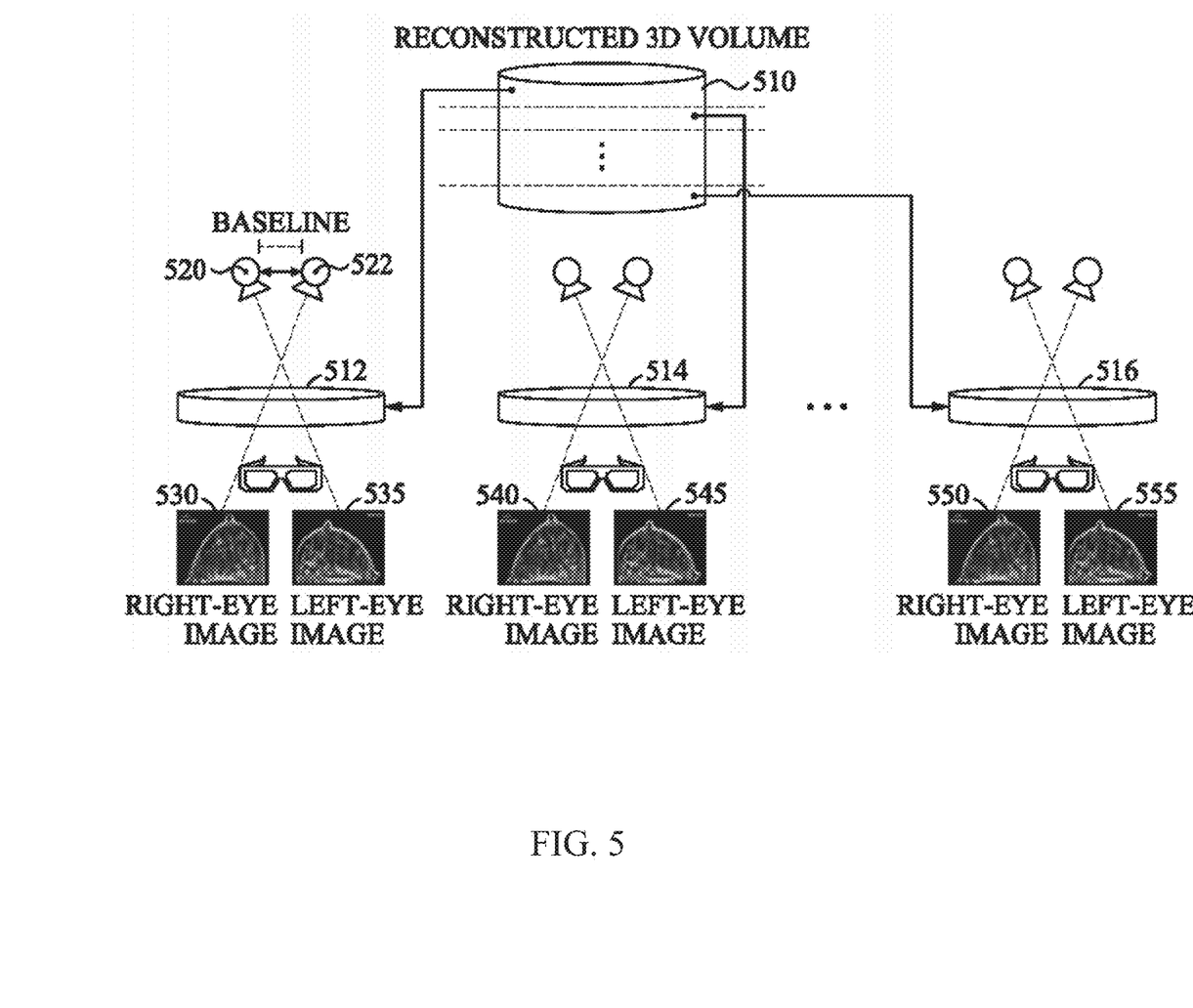
FIG. 5 is a diagram which illustrates a method for providing a stereoscopic image with respect to a partial volume, according to one or more exemplary embodiments.

FIG. 5 is a diagram which illustrates a method for providing a stereoscopic image with respect to a partial volume, according to one or more exemplary embodiments.

A reconstructed 3D volume 510 may represent a full volume of the object 190 which is generated in operation 240 of FIG. 2.

The controller 130 may generate one or more partial volumes by dividing the full volume into at least one plane in parallel with a detector plane. The detector plane may indicate a plane in parallel with a detector or a plane on which a detection surface of the X-ray detector 120 appears. For example, each of at least one partial volume may be a portion of the full volume. The at least one partial volume may have an identical initial size or different initial sizes.

Referring to FIG. 5, a first partial volume 512, a second partial volume 514, and an Nth partial volume 516 are provided as partial volumes. In particular, N may correspond to the number of partial volumes and denote an integer which is greater than or equal to 1. The 3D volume described with reference to FIG. 2 may indicate one of the at least one partial volume.

Each of the plurality of second projection images may be a projection image with respect to one of the at least one partial volume. Each of the plurality of second projection images may be a virtual projection image which represents a partial volume which is projected at a different angle. The controller 130 may select, from among the plurality of second projection images, a left image and a right image in order to provide a perception of 3D depth to the user. The controller 130 may provide the selected left image and right image to a left eye and a right eye of the user, respectively, via the output unit 140. The user may observe a projection image of a partial volume with the perception of depth because each respective eye of the user views a different image.

The 3D image providing apparatus 100 may decrease depth blurring in a projection image by providing the projection image with respect to a partial volume. In particular, depth blurring may indicate that a projection image is scattered into a z-axial direction of the partial volume. Depth blurring may cause degradation in a resolution of the projection image. The z-axial direction may be a direction which corresponds to a thickness of the partial volume.

The 3D image providing apparatus 100 may decrease a perception of overlapping between tissues by providing a projection image with respect to a partial volume. Further, the 3D image providing apparatus 100 may perform reprojection only with respect to the partial volume and thus, may decrease an artifact which may occur due to recovery of a volume.

The 3D image providing apparatus 100 may provide information associated with a depth of tissue to the user by providing a 3D projection image. The user may perform a diagnosis with respect to a person to be measured by using a relatively small number of slabs, as compared to a case in which a conventional slice image is used. In the case of using the conventional slice image, the user may have difficulty in identifying a twisted tissue on a detector plane due to depth blurring. According to one or more exemplary embodiments, depth blurring may be mitigated or eliminated as an issue in a projection image with respect to a partial volume.

FIG. 5 illustrates a right-eye image to be viewed by using a right eye of the user and a left-eye image to be viewed by using a left eye of the user. The right-eye image may be a second projection image which corresponds to a first position 522 from among the plurality of second projection images. The first position 522 may be a position of the X-ray source 110 which corresponds to a position of the right eye of the user. The left-eye image may be a second projection image which corresponds to a second position 520 from among the plurality of second projection images. The second position 520 may be a position of the X-ray source 110 which corresponds to a position of the left eye of the user.

A right-eye image 530 and a left-eye image 535 may be provided with respect to the first partial volume 512. A right-eye image 540 and a left-eye image 545 may be provided with respect to the second partial volume 514. Further, a right-eye image 550 and a left-eye image 555 may be provided with respect to the Nth partial volume 516.

The controller 130 may select a left-eye image and a right-eye image from among the plurality of second projection images based on any one or more from among a variety of criteria.

For example, the controller 130 may adjust a left image and a right image such that a recovery of the 3D volume is recognizable by viewing the left image and the right image based on a length of a baseline of the user. In particular, adjusting of the left image and the right image may indicate selecting which second projection images are to be used as the left image and the right image from among the plurality of second projection images.

For example, the controller 130 may adjust a left image and a right image such that a 3D volume is recognizable by viewing the left image and the right image based on a thickness of the 3D volume. In particular, the thickness of the 3D volume may be a maximum depth that the user may perceive with respect to the 3D volume.

The baseline may indicate an interval between the left image and the right image, and may also indicate a disparity of the user. The interval and the thickness may be in inverse proportion to each other. The controller 130 may adjust a baseline between the left image and the right image so that the user may feel the 3D effect based on the thickness of the 3D volume. The controller 130 may adjust the interval and the number of second projection images created via view interpolation based on the adjusted baseline. For example, the controller 130 may select the left image and the right image so that the interval between the left image and the right image may be narrowed according to an increase in the thickness of the 3D volume.

The 3D image providing method according to the above-described exemplary embodiments may be recorded in non-transitory computer-readable media which include program instructions in order to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as compact disk-read-only memory (CD ROM) disks and digital versatile disks (DVDs); magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described exemplary embodiments, or vice versa.

Although a few exemplary embodiments have been shown and described, exemplary embodiments are not limited thereto. Instead, it will be appreciated by those skilled in the art that changes may be made to these exemplary embodiments without departing from the principles and spirit of the present disclosure, the scope of which is defined by the claims and their equivalents.

What is claimed is:

1. A method for providing a three-dimensional (3D) image, the method comprising:
   acquiring a plurality of first projection images which are created by detecting, by using an X-ray detector, X-rays which are emitted from an X-ray source toward an object;
   generating a 3D volume which represents the object by using the plurality of first projection images;
   creating a plurality of second projection images by applying a forward projection to the 3D volume; and
   displaying the plurality of second projection images by using a 3D display.

2. The method of claim 1, wherein:
   the generating the 3D volume comprises:
   generating a full volume of the object by using the plurality of first projection images; and
   dividing the full volume into at least one partial volume, wherein the 3D volume is selected from the at least one partial volume.

3. The method of claim 2, wherein the dividing the full volume comprises using at least one plane in parallel with a detector plane.

4. The method of claim 1, wherein the plurality of first projection images is created by detecting, by using the X-ray detector, the X-rays which are emitted from the X-ray source toward the object at an angle from within a predetermined angular range.

5. The method of claim 4, wherein at least one of a number of first projection images which comprise the plurality of first projection images and the predetermined angular range is determined based on a radiation dose which relates to the object.

6. The method of claim 1, wherein:
the creating the plurality of second projection images comprises creating at least one reprojection image by applying at least one of the forward projection and an interpolation to at least one of the plurality of first projection images, and
the plurality of second projection images comprises the plurality of first projection images and the at least one reprojection image.

7. The method of claim 1, wherein the plurality of second projection images comprises a left image which is observable by using a left eye of a user and a right image which is observable by using a right eye of the user.

8. The method of claim 7, wherein each of the left image and the right image is adjusted such that the 3D volume is recognizable by viewing the left image and the right image based on a baseline length of the user.

9. The method of claim 7, wherein each of the left image and the right image is adjusted such that the 3D volume is recognizable by viewing the left image and the right image based on a thickness of the 3D volume.

10. A non-transitory computer-readable medium storing a program which implements the method of claim 1.

11. An apparatus for providing a three-dimensional (3D) image, the apparatus comprising:
an X-ray source which emits X-rays toward an object;
an X-ray detector which detects the emitted X-rays;
a controller which generates a 3D volume which represents the object by using a plurality of first projection images that is created by detecting, by using the X-ray detector, the X-rays emitted from the X-ray source toward the object at different angles, and which creates a plurality of second projection images by applying a forward projection to the 3D volume; and
an output unit which outputs the plurality of second projection images.

12. The apparatus of claim 11, wherein:
the controller generates a full volume of the object by using the plurality of first projection images and divides the full volume into at least one partial volume, and the 3D volume is selected from the at least one partial volume.

13. The apparatus of claim 12, wherein the controller generates the at least one partial volume by dividing the full volume by using at least one plane in parallel with a detector plane.

14. The apparatus of claim 11, wherein the plurality of first projection images is created by detecting, by using the X-ray detector, the X-rays which are emitted from the X-ray source toward the object at an angle from within a predetermined angular range.

15. The apparatus of claim 14, wherein the controller determines at least one of a number of first projection images which comprise the plurality of first projection images and the predetermined angular range based on a radiation dose which relates to the object.

16. The apparatus of claim 11, wherein:
the controller creates at least one reprojection image by applying at least one of the forward projection and an interpolation to at least one of the plurality of first projection images, and
the plurality of second projection images comprises the plurality of first projection images and the at least one reprojection image.

17. The apparatus of claim 11, wherein the plurality of second projection images comprises a left image which is observable by using a left eye of a user and a right image which is observable by using a right eye of the user.

18. The apparatus of claim 17, wherein the controller adjusts each of the left image and the right image such that the 3D volume is recognizable by viewing the left image and the right image based on a baseline length of the user.

19. The apparatus of claim 17, wherein the controller adjusts each of the left image and the right image such that the 3D volume is recognizable by viewing the left image and the right image based on a thickness of the 3D volume.

20. A method for facilitating a diagnosis to be performed with respect to a body part, the method comprising:
detecting x-rays which are emitted toward the body part;
using the detected x-rays to obtain at least one first projection image of the body part;
using the at least one first projection image to generate a three-dimensional representation of the body part;
applying a forward projection to the three-dimensional representation of the body part; and
displaying a result of the applying the forward projection.

* * * * *